(12) United States Patent
Kaneko et al.

(10) Patent No.: US 9,638,645 B2
(45) Date of Patent: *May 2, 2017

(54) DETERIORATION ANALYSIS METHOD

(75) Inventors: Fusae Kaneko, Kobe (JP); Hiroyuki Kishimoto, Kobe (JP)

(73) Assignee: SUMITOMO RUBBER INDUSTRIES, LTD., Kobe-Shi (JP)

( * ) Notice: Subject to any disclaimer, the term of this patent is extended or adjusted under 35 U.S.C. 154(b) by 977 days.

This patent is subject to a terminal disclaimer.

(21) Appl. No.: 13/881,158

(22) PCT Filed: Aug. 9, 2011

(86) PCT No.: PCT/JP2011/068139
§ 371 (c)(1),
(2), (4) Date: Apr. 24, 2013

(87) PCT Pub. No.: WO2012/081278
PCT Pub. Date: Jun. 21, 2012

(65) Prior Publication Data
US 2013/0226470 A1    Aug. 29, 2013

(30) Foreign Application Priority Data

Dec. 16, 2010   (JP) .................. 2010-281017
Jul. 29, 2011    (JP) .................. 2011-167131

(51) Int. Cl.
G01N 23/00     (2006.01)
G01N 33/44     (2006.01)
G01N 23/06     (2006.01)
G01N 23/083    (2006.01)

(52) U.S. Cl.
CPC .......... G01N 23/00 (2013.01); G01N 23/063 (2013.01); G01N 23/083 (2013.01); G01N 33/445 (2013.01); G01N 2223/627 (2013.01)

(58) Field of Classification Search
USPC ....................... 702/22; 436/73, 85
See application file for complete search history.

(56) References Cited

U.S. PATENT DOCUMENTS

2006/0120508 A1   6/2006   Chen et al.
2013/0226470 A1   8/2013   Kaneko et al.

FOREIGN PATENT DOCUMENTS

| | | |
|---|---|---|
| CN | 1829910 A | 9/2006 |
| EP | 2 653 858 A1 | 10/2013 |
| JP | 2000-137008 A | 5/2000 |
| JP | 2004-99738 A | 4/2004 |

(Continued)

OTHER PUBLICATIONS

Dhez et al., "Calibrated NEXAFS spectra of some common polymers", Journal of Electron Spectroscopy and Related Phenomena, vol. 128, 2003, pp. 85-96.

(Continued)

*Primary Examiner* — Lam Nguyen
(74) *Attorney, Agent, or Firm* — Birch, Stewart, Kolasch & Birch, LLP

(57) ABSTRACT

The present invention provides deterioration analysis method which allows a detailed analysis of deterioration, especially deterioration of surface conditions, of a polymer material. The present invention relates to a deterioration analysis method, including irradiating a polymer material with high intensity X-rays, and measuring X-ray absorption while varying the energy of the X-rays, to analyze deterioration of the polymer.

4 Claims, 4 Drawing Sheets

(56) References Cited

FOREIGN PATENT DOCUMENTS

| JP | 2012-78421 A | 4/2012 |
|---|---|---|
| JP | 2012-141278 A | 7/2012 |
| WO | WO 2004/111624 A2 | 12/2004 |
| WO | WO 2012/081278 A1 | 6/2012 |

OTHER PUBLICATIONS

Ikeda et al., "Study on Vulcanization and Properties of Styrene-Butadiene Rubber by Synchrotron X-ray and Small-Angle Neutron Scattering", Elastomer Toronkai Koen Yoshishu, Dec. 2, 2010, pp. 155-156 (with English Abstract).

Klein et al., "Systematic Oxidation of Polystyrene by Ultraviolet-Ozone, Characterized by Near-Edge X-ray Absorption Fine Structre and Contact Angle", Langmuir, vol. 24, No. 15, 2008, pp. 8187-8197.

Minota et al., "Styrene-Butadiene Kyojugo Gomu no Karyu ni Kansuru Kenkyu", The Society of Rubber Industry, Japan Kenkyu Happyo Koenkai Koen Yoshi, May 20, 2010, p. 16.

Mukherjee et al., "Onset Kinetics of Thermal Degradation of Ultrathin Polyacrylamide Films", Macromolecules, vol. 42, No. 20, 2009, pp. 7889-7896.

Okajima et al., "Analysis of Polymer Surfaces Using XAFS", Hyomen Kagaku (Surface Science), vol. 23, No. 6, 2002, pp. 359-366 (with English Abstract).

Coffey et al., Characterization of the Effects of Soft X-Ray Irradiation on Polymers, Journal of Election Spectroscopy and Related Phenomena, 2002, pp. 65-78, vol. 122, XP055115895.

Richard, et al., X-Ray Absorption Near Edge Spectroscopy (XANES) Study of Thermostable POlyphenylquinoxaline (PPQ) Polymer prior to Cu Thin Films Deposition, Le Journal de Physique IV, Nov. 1993, pp. 789-792, vol. 3, No. C7, XP055115894.

Winesett, et al., Application of Scanning Transmission X-Ray Microscopy to the Rubber Industry, Rubber Chemistry and Technology, Sep. 2003, pp. 803-811, vol. 76, No. 4, XP055115896.

Kaneko et al., "Hoshako o Mochiita Gomu no Kagaku Jotai Bunseki (Chemical State Analysis of Rubber Using Radiation)," The Society of Rubber Industry, Japan Kenkyu Happyo Koenkai Koen Yoshi, May 30, 2011, pp. 39 (2 pages total).

Mitra et al., "Chemical Degradation of Crosslinked Ethylene-propylene-diene Rubber in an Acidic Environment. Part I. Effect on Accelerated Sulphur Crosslinks", Polymer Degradation and Stability, vol. 91, 2006, pp. 69-80.

Winter et al., "The Thermal Ageing of Poly(3,4-ethylenedioxythiophene). An Investigation by X-ray Absorption and X-ray Photoelectron Spectroscopy," Chemical Physics, vol. 194, 1995, pp. 207-213.

International Preliminary Report on Patentability, English translation of the Written Opinion of the International Searching Authority and International Search Report (forms PCT/IB/373, PCT/ISA/237 and PCT/ISA/210), issued May 6, 2014, for International Application No. PCT/JP2012/078421.

International Search Report (form PCT/ISA/210), issued Nov. 15, 2011, for International Application No. PCT/JP2011/068139, along with an English translation.

DETERIORATION ANALYSIS METHOD

TECHNICAL FIELD

The present invention relates to a deterioration analysis method for analysis of deterioration of a polymer material.

BACKGROUND ART

For analyzing a change in chemical state of a polymer material containing at least one diene rubber caused by deterioration, for example, an infrared spectroscopy (FT-IR), nuclear magnetic resonance analysis (NMR), and X-ray photoelectron spectroscopy (XPS) and the like are commonly employed. Though FT-IR or NMR allows a detailed analysis of the chemical state, the obtained information is bulk information and therefore it is difficult to analyze in detail the chemical state after deterioration which starts at a sample surface.

On the other hand, XPS is a surface-sensitive method and is therefore thought to be effective for analysis of a change in chemical state caused by deterioration. As one example of analysis and evaluation of deterioration by XPS, FIG. 1 shows the results of XPS measurement of the 1s orbital of carbon in fresh butadiene rubber (BR), ozone-deteriorated BR, and oxygen-deteriorated BR (carbon K-shell absorption edge of BR).

As shown in FIG. 1, in the XPS measurement, the peak of C═C bond (double bond) and the peak of C—C bond (single bond) overlap each other at around 285 eV, and therefore the chemical states of the different groups cannot be distinguished. Hence, it is difficult to determine the amount of C═C bonds (double bonds) that is reduced by deterioration. Moreover, in FIG. 2 showing the results of XPS measurement of the oxygen K shell absorption edge of BR, no difference is found in the spectra between the ozone-deteriorated BR and oxygen-deteriorated BR. Hence, a detailed analysis of deterioration by XPS is difficult.

Meanwhile, measurement of X-ray absorption spectra of polymers has also been carried out as disclosed in Non Patent Literatures 1 to 3. However, no disclosure is found in any literatures including these non patent literatures that deterioration factors can be distinguished based on the X-ray absorption spectra.

CITATION LIST

Non Patent Literature

Non Patent Literature 1: O. Dhez, H. Ade, S. G. Urquhart. J. Electron Spectrosc. Relat. Phenom., 2003, 128, 85-96
Non Patent Literature 2: Robert J. Klein, Daniel A. Fischer, and Joseph L. Lenhart. Langmuir., 2008, 24, 8187-8197
Non Patent Literature 3: Toshihiro Okajima, Hyomen kagaku (Surface Science), 2002, Vol. 23, No. 6, 356-366

SUMMARY OF INVENTION

Technical Problem

The present invention aims to provide a deterioration analysis method which can solve the above problems and allows a detailed analysis of deterioration, especially deterioration of surface conditions, of a polymer material.

Solution to Problem

The present invention relates to a deterioration analysis method, including irradiating a polymer material with high intensity X-rays, and measuring X-ray absorption while varying the energy of the X-rays, to analyze deterioration of the polymer.

The polymer material is preferably a rubber material containing at least one diene rubber, or a composite material combining the rubber material and at least one resin.

The high intensity X-rays preferably have a number of photons of $10^7$ (photons/s) or more and a brilliance of $10^{10}$ (photons/s/mrad$^2$/mm$^2$/0.1% bw) or more. Also, an energy range scanned with the high intensity X-rays is preferably 4000 eV or less.

The deterioration analysis method preferably includes: calculating normalization constants $\alpha$ and $\beta$ using Equation 1 below based on X-ray absorption spectra obtained by scanning over a required range of high intensity X-ray energies at the carbon K-shell absorption edge within the range of 260 to 400 eV; performing waveform separation of the X-ray absorption spectra at the carbon K-shell absorption edge corrected with the normalization constants $\alpha$ and $\beta$ to obtain peak areas attributed to $\pi^*$ transition at around 285 eV; and determining a degree of deterioration using Equation 2 below with the obtained peak areas:

[total area of X-ray absorption spectrum over measurement range of sample before deterioration]×$\alpha$=1, and

[total area of X-ray absorption spectrum over measurement range of sample after deterioration]×$\beta$=1; and     (Equation 1)

[1−[(peak area of $\pi^*$ after deterioration)×$\beta$]/[(peak area of $\pi^*$ before deterioration)×$\alpha$]]×100=degree (%) of deterioration.     (Equation 2)

In the deterioration analysis method, peak intensities may be used instead of the peak areas.

The deterioration analysis method preferably includes: performing waveform separation of an X-ray absorption spectrum at the oxygen K-shell absorption edge obtained by scanning over a range of high intensity X-ray energies of 500 to 600 eV; and calculating contribution rates of oxygen deterioration and ozone deterioration using Equation 3 below, wherein the oxygen deterioration corresponds to a peak on the low energy side with a peak top energy in the range of 532 to 532.7 eV, and the ozone deterioration corresponds to a peak on the high energy side with a peak top energy in the range of 532.7 to 534 eV:

[peak area of oxygen deterioration]/[(peak area of ozone deterioration)+(peak area of oxygen deterioration)]×100=contribution rate (%) of oxygen deterioration, and

[peak area of ozone deterioration]/[(peak area of ozone deterioration)+(peak area of oxygen deterioration)]×100=contribution rate (%) of ozone deterioration.     (Equation 3)

In the deterioration analysis method, peak intensities may be used instead of the peak areas.

The deterioration analysis method preferably includes: determining a normalization constant $\gamma$ using Equation 4 below based on an X-ray absorption spectrum at the carbon K-shell absorption edge after deterioration; and correcting a total peak area of the oxygen K-shell absorption edge with the normalization constant $\gamma$ to determine the amount of oxygen and ozone bonded to the polymer material:

[total area of X-ray absorption spectrum at carbon K-shell absorption edge]×$\gamma$=1, and

[peak area of oxygen K-shell absorption edge]×
γ=amount (index) of oxygen and ozone bonded. (Equation 4)

Advantageous Effects of Invention

Since the deterioration analysis method according to the present invention includes irradiating a polymer material with high intensity X-rays, and measuring X-ray absorption while varying the energy of the X-rays, to analyze deterioration of the polymer, the method can analyze in detail the deterioration, especially deterioration of surface conditions, of a polymer material. Accordingly, with regard to the deterioration of a polymer material, the degree (%) of deterioration, the contribution rates of oxygen deterioration and ozone deterioration, and the amount of oxygen and ozone bonded to the polymer material (deterioration indicator) can be measured.

DESCRIPTION OF EMBODIMENTS

Figure 1:
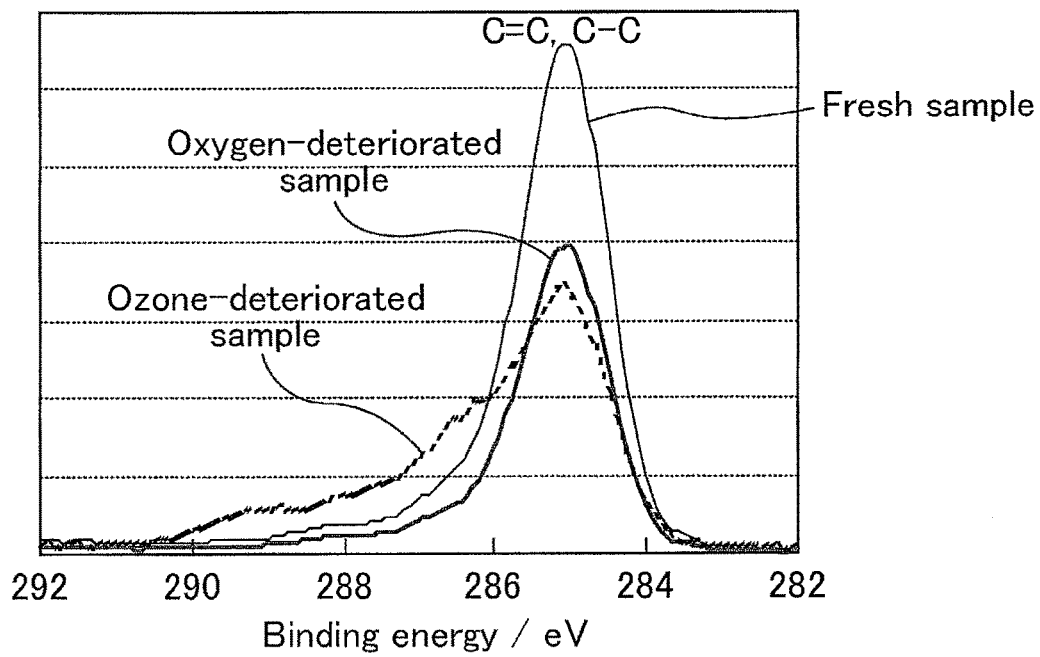
FIG. 1 is a graph showing the results of XPS measurement of the 1 s orbital of carbon in fresh butadiene rubber (BR), ozone-deteriorated BR, and oxygen-deteriorated BR.
Figure 2:
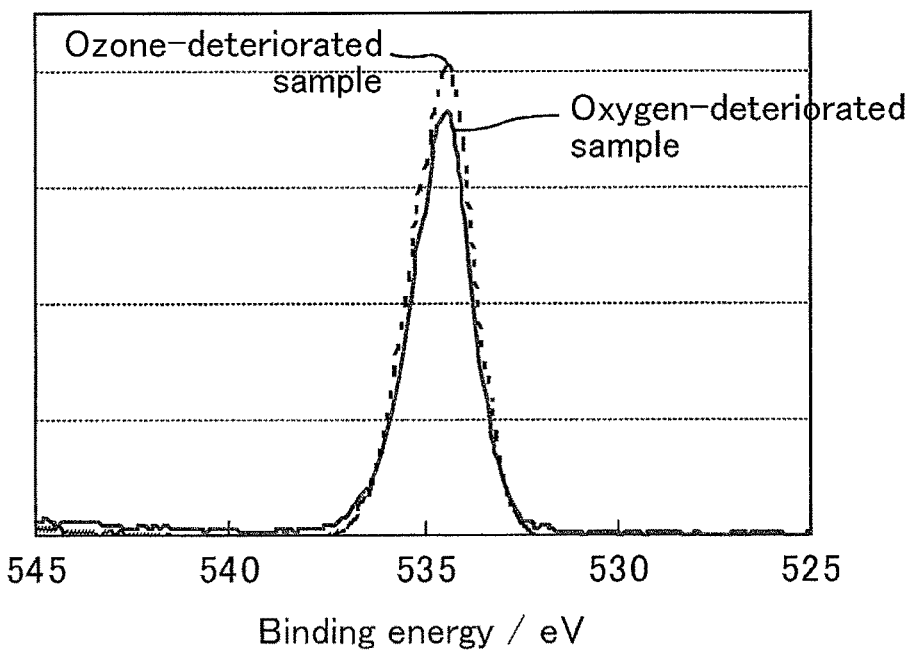
FIG. 2 is a graph showing the results of XPS measurement of the oxygen K-shell absorption edge in ozone-deteriorated butadiene rubber and oxygen-deteriorated butadiene rubber.

The deterioration analysis method of the present invention includes irradiating a polymer material with high intensity X-rays, and measuring X-ray absorption while varying the energy of the X-rays, to analyze deterioration of the polymer. Known deterioration factors of polymer materials such as rubber include deterioration of polymer molecular chains and crosslinked structures by ultraviolet light, oxygen, ozone, heat and the like. To improve the resistance to deterioration, it is important to know what factor is responsible and how the polymer molecular chains and crosslinked structures then change.

In this respect, the deterioration analysis method focuses on the use of high intensity X-rays to analyze the chemical state in greater detail than the conventional methods such as FT-IR, NMR, Raman scattering spectroscopy, and XPS. In this method, while the energy of high intensity X-rays is varied, fresh and deteriorated polymer materials are irradiated with the X-rays to measure the X-ray absorption, and then the obtained spectra are compared, whereby the deterioration of the deteriorated polymer material can be analyzed.

Specifically, a method may be employed in which an X-ray absorption spectrum around the absorption edge of a specific target element is measured using high intensity X-rays (NEXAFS: Near Edge X-ray Absorption Fine Structure). Since the soft X-ray region includes absorption edges of light elements, the chemical state of soft materials can be analyzed in detail.

Since X-ray energy is used for scanning in the NEXAFS method, a continuous X-ray generator is needed as the light source. For a detailed analysis of the chemical state, an X-ray absorption spectrum with high S/N and S/B ratios needs to be measured. For this reason, a synchrotron is suitably used in the NEXAFS measurement because it emits X-rays having a brilliance of at least $10^{10}$ (photons/s/mrad$^2$/mm$^2$/0.1% bw) and is a continuous X-ray source. It is to be noted that the symbol bw indicates a band width of X-rays emitted from a synchrotron.

The brilliance (photons/s/mrad$^2$/mm$^2$/0.1% bw) of the high intensity X-rays is preferably $10^{10}$ or more, and more preferably $10^{12}$ or more. The upper limit thereof is not particularly limited, and the X-ray intensity used is preferably low enough not to cause radiation damage.

The number of photons (photons/s) of the high intensity X-rays is preferably $10^7$ or more, and more preferably $10^9$ or more. The upper limit thereof is not particularly limited, and the X-ray intensity used is preferably low enough not to cause radiation damage.

The energy range scanned with the high intensity X-rays is preferably 4000 eV or less, more preferably 1500 eV or less, and still more preferably 1000 eV or less. With an energy range exceeding 4000 eV, the deterioration of a target polymer composite material may not be analyzed. The lower limit is not particularly limited.

The measurement can be carried out as follows. A sample placed in an ultra-high vacuum is irradiated with soft X-rays so that photoelectrons are emitted. Then electrons flow from the ground to the sample so as to compensate for the emitted photoelectrons, and this sample current is measured. Accordingly, such measurement is surface-sensitive but can only measure samples that do not produce gas in vacuo and are electrically conductive. Therefore, in the past, crystals and molecular adsorption have been mainly studied through the measurement, whereas rubber samples that are likely to produce gas and are insulating materials have hardly been studied.

However, the ESCA method, which is similarly surface-sensitive, observes the inner shells of an atom and thus is difficult to distinguish the deteriorations of a polymer in detail. In contrast, the NEXAFS method observes the outer shells of an atom which are affected by the reaction between atoms, and thus allows greater reflection of the impact of an element bonded to the target element than the ESCA method. Therefore, the present inventors have considered that the NEXAFS method can distinguish individual molecular states and thus can distinguish deterioration factors, thereby completing the present invention.

More specifically, the measurement can be conducted by the following method.

A sample mounted on a sample holder is placed in a vacuum chamber for X-ray absorptiometry. Then the sample is irradiated with continuous X-rays that are emitted from a synchrotron and subsequently monochromatized with a monochromator. At that time, secondary electrons and photoelectrons escape from the sample surface into vacuum, and then electrons are replenished from the ground to compensate for the loss of electrons. Then, the X-ray absorption (μL) is calculated using Equation 5 below, wherein the X-ray absorption intensity I represents a current flowing from the ground, and the incident X-ray intensity $I_0$ represents a current from a gold mesh provided in an optical system of a beamline (electron yield method). It should be noted that the equation of Lambert-Beer is applicable to the method, and Equation 5 is thought to hold approximately in the case of the electron yield method:

$I_0(E)/I(E)=\exp(\mu L)\approx\mu L$ ($E$: energy of X-rays, $L$: thickness of sample, $\mu$: absorption coefficient). (Equation 5)

The following three methods are typically used as the NEXAFS measurement. In examples of the present invention, the electron yield method is employed but is not intended to limit the scope of the invention. Various detection methods may be employed and may be combined for simultaneous measurement.

(Transmission Method)

This is a method of detecting the intensity of the X-rays having passed through a sample. For measurement of the intensity of transmitted light, for example, a photodiode array detector may be used.

(Fluorescence Method)

This is a method of detecting fluorescent X-rays generated when a sample is irradiated with X-rays. In the case of the transmission method, if the X-ray absorption of an element contained in a small amount in a sample is measured, then a spectrum with a poor S/B ratio is obtained because the signal is small and the background is high due to X-ray absorption by an element contained in a large amount in the sample. In contrast, in the case of the fluorescence method (especially when an energy dispersive detector or the like is used), only the fluorescent X-rays from the target element can be measured and thus the element contained in a large amount has a small influence. Hence, the method is effective in order to measure the X-ray absorption spectrum of an element contained in a small amount. In addition, since fluorescent X-rays have high penetrating power (low interaction with substances), fluorescent X-rays generated inside the sample can be detected. Hence, the method is the second most suitable method for obtaining bulk information after the transmission method.

(Electron Yield Method)

This is a method of detecting a current flowing when a sample is irradiated with X-rays. Thus, the sample needs to be an electrically conductive material. Since polymer materials are insulating materials, X-ray absorption measurement of a polymer material has mostly been carried out by putting a very thin layer of a sample on a substrate by deposition, spin-coating or the like. In the present invention, when a polymer material is processed (cut) with a microtome to 100 μm or less, preferably to 10 μm or less, more preferably to 1 μm or less, and still more preferably to 500 nm or less, high S/B and S/N ratios can be achieved through the measurement.

The electron yield method features surface sensitivity (information from the sample surface to a depth of approximately several nanometers). Irradiation of a sample with X-rays causes escape of electrons from elements. Since electrons have a great interaction with substances, their mean free path in a substance is short.

The X-ray absorption spectra of a polymer material can be measured by the electron yield method and then analyzed to assay the degree (%) of deterioration, the contribution rates (%) of oxygen deterioration and ozone deterioration, and the amount of oxygen and ozone bonded (deterioration indicator). These assays are described below.

The deterioration analysis method may include: calculating normalization constants α and β using Equation 1 below based on X-ray absorption spectra obtained by scanning over a required range of high intensity X-ray energies at the carbon K-shell absorption edge within the range of 260 to 400 eV; performing waveform separation of the X-ray absorption spectra at the carbon K-shell absorption edge corrected with the normalization constants α and β to obtain peak areas attributed to π* transition at around 285 eV; and determining a degree of deterioration using Equation 2 below with the obtained peak areas:

[total area of X-ray absorption spectrum over measurement range of sample before deterioration]× α=1, and

[total area of X-ray absorption spectrum over measurement range of sample after deterioration]× β=1; and (Equation 1)

[1−[(peak area of π* after deterioration)×β]/[(peak area of π* before deterioration)×α]]×100=degree of deterioration (%). (Equation 2)

In this manner, the degree (%) of deterioration of a polymer after deterioration can be obtained to allow analysis of the deterioration rate. In the method for determining the degree of deterioration, the range of high intensity X-ray energies is preferably 260 to 350 eV. In the method for determining the degree of deterioration, the background is assessed based on a slope before the absorption edge and subtracted, prior to the calculation of Equation 1.

In the method for determining the degree of deterioration, the total area of the X-ray absorption spectrum in Equation 1 is the integral of the spectrum over a measurement range. The energy range can be changed according to the measurement conditions and the like.

The method for determining the degree of deterioration is more specifically described using an example in which fresh BR, a sample subjected to ozone deterioration for seven hours, a sample subjected to oxygen deterioration for a week are used.

Figure 3:
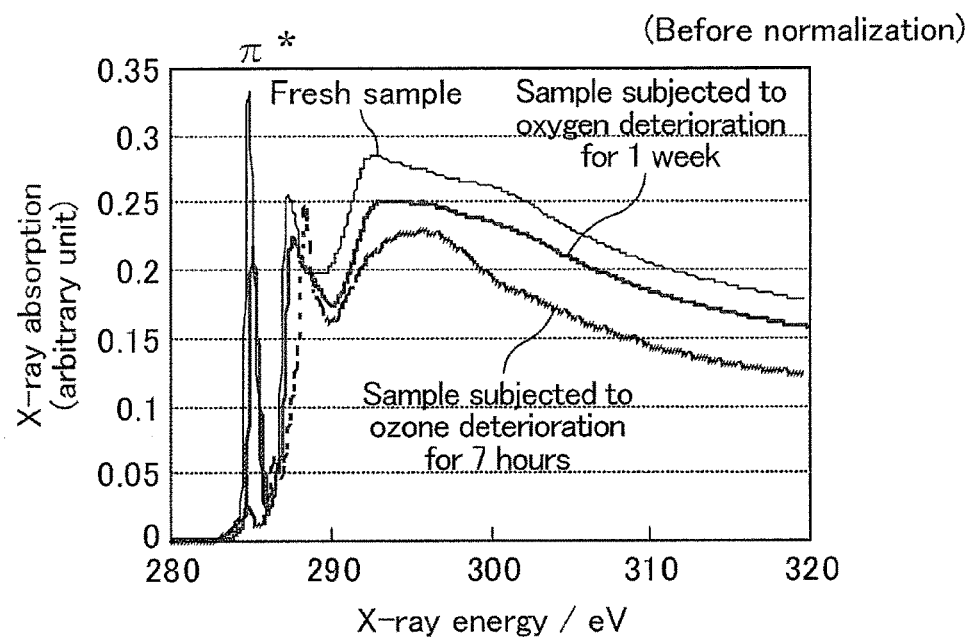
FIG. 3 is a graph (before normalization) showing the results of NEXAFS measurement of the carbon K-shell absorption edge in fresh butadiene rubber, a sample subjected to ozone deterioration for seven hours, and a sample subjected to oxygen deterioration for a week.

FIG. 3 shows the results of NEXAFS measurement of the carbon K-shell absorption edge in these samples. As shown in FIG. 3, deteriorated samples each have a smaller π* peak at around 285 eV than the fresh sample; however, the NEXAFS method is difficult to perform an absolute measurement because subtle changes in the distance from the light source to the sample and the like affect the magnitude of the X-ray absorption spectrum. For this reason, the results of NEXAFS measurement of the carbon K-shell absorption edge cannot be simply compared between samples.

For comparison between the X-ray absorption spectra of the measured samples, normalization is carried out as follows (the X-ray absorption spectrum of each sample is corrected for direct comparison). Since the amount of carbon shell X-ray absorption is not changed before and after deterioration, the peak area of the carbon K-shell absorption edge is normalized to 1 using Equation 1. In other words, normalization constants α and β are first calculated using Equation 1 based on the X-ray absorption spectra before normalization, and then the spectra are corrected (normalized) by multiplying the X-ray absorption spectra before normalization by α and β, whereby the π* peaks of the samples can be directly compared.

Figure 4:
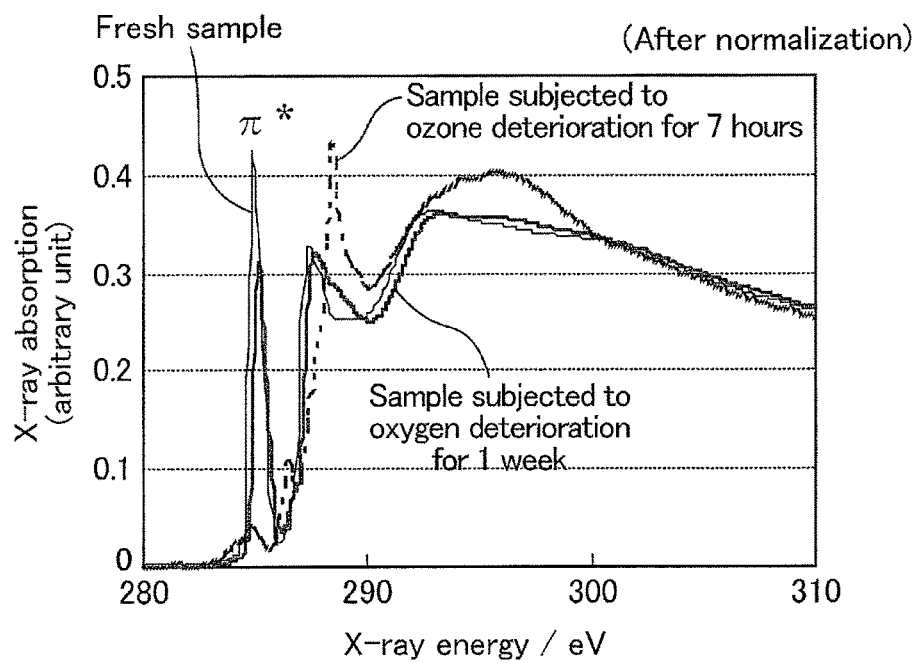
FIG. 4 is a graph (after normalization) showing the results of NEXAFS measurement of the carbon K-shell absorption edge in fresh butadiene rubber, a sample subjected to ozone deterioration for seven hours, and a sample subjected to oxygen deterioration for a week.

FIG. 4 shows the thus-obtained spectra at the carbon K-shell absorption edge after normalization. The degree of deterioration is determined using Equation 2 based on the normalized spectra. The degree of deterioration is the π* peak reduction from before to after deterioration, and indicates the deterioration rate (%) of a sample.

In the method for determining the degree of deterioration, the degree of deterioration can be similarly determined when peak intensities are used instead of the peak areas in Equation 2.

Other examples of the deterioration analysis method include a method that includes: performing waveform separation of an X-ray absorption spectrum at the oxygen K-shell absorption edge obtained by scanning over a range of high intensity X-ray energies of 500 to 600 eV; and calculating contribution rates of oxygen deterioration and ozone deterioration using Equation 3 below, wherein the oxygen deterioration corresponds to a peak on the low energy side with a peak top energy in the range of 532 to 532.7 eV, and the ozone deterioration corresponds to a peak on the high energy side with a peak top energy in the range of 532.7 to 534 eV:

[peak area of oxygen deterioration]/[(peak area of ozone deterioration)+(peak area of oxygen deterioration)]×100=contribution rate (%) of oxygen deterioration, and

[peak area of ozone deterioration]/[(peak area of ozone deterioration)+(peak area of oxygen deterioration)]×100=contribution rate (%) of ozone deterioration.      (Equation 3)

In this manner, the contribution rates (%) of oxygen deterioration and ozone deterioration in a polymer material after deterioration can be obtained to allow analysis of the contribution rate of each deterioration factor. In the method for calculating the contribution rates, the background is assessed based on a slope before the absorption edge and subtracted, prior to the calculation of Equation 3.

The method for calculating the contribution rates is more specifically described using an example in which fresh BR, a sample subjected to ozone deterioration for seven hours, and a sample subjected to oxygen deterioration for a week are used.

Figure 5:
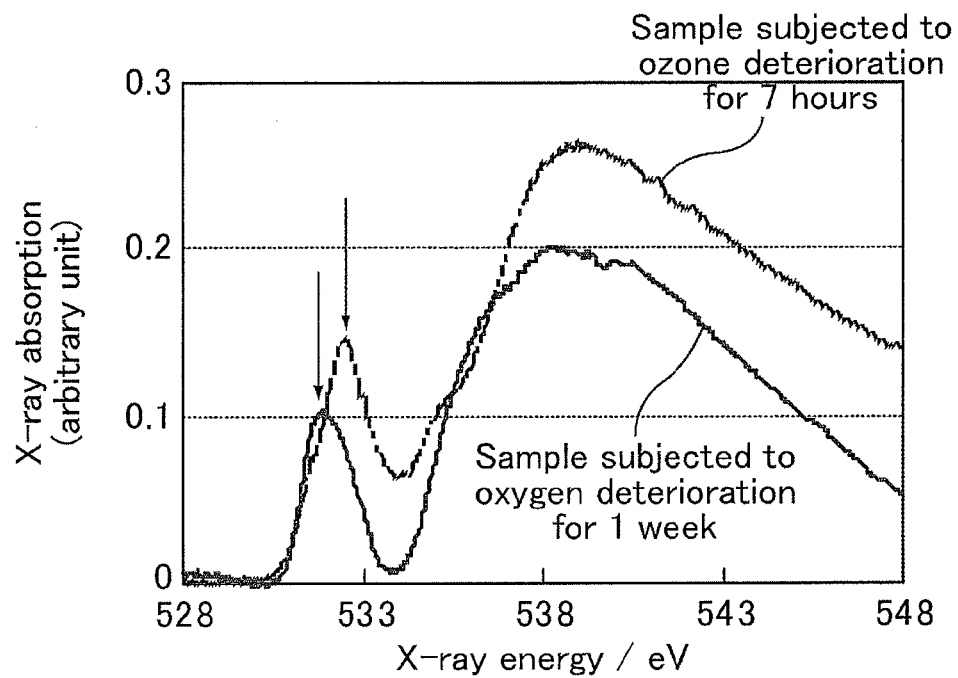
FIG. 5 is a graph showing the results of NEXAFS measurement around the oxygen K-shell absorption edge in a butadiene rubber sample subjected to ozone deterioration for seven hours and a sample subjected to oxygen deterioration for a week.

First, FIG. 5 shows the results of NEXAFS measurement around the oxygen K-shell absorption edge in the fresh BR, the sample subjected to ozone deterioration for seven hours, and the sample subjected to oxygen deterioration for a week as shown in FIG. 1. As shown in the figure, the ozone-deteriorated sample has a peak at 532.7 to 534 eV, and the oxygen-deteriorated sample has a peak at 532 to 532.7 eV. It is found out that, of these two peaks, the peak on the high energy side is attributed to ozone deterioration and the peak on the low energy side is attributed to oxygen deterioration.

Figure 6:
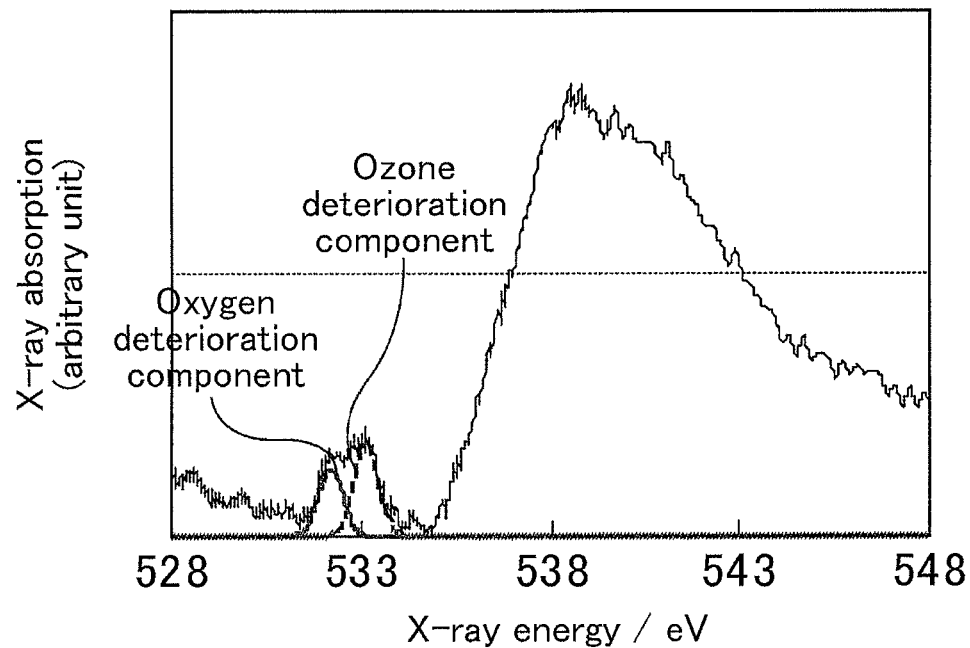
FIG. 6 is a graph showing the results of NEXAFS measurement around the oxygen K-shell absorption edge in a butadiene rubber sample subjected to complex deterioration (both oxygen deterioration and ozone deterioration).

FIG. 6 shows the results of NEXAFS measurement in a sample subjected to complex deterioration (both oxygen deterioration and ozone deterioration). As shown in FIG. 6, a peak with two shoulders was detected at 532 to 534 eV. This is thought to be due to overlapping of the peak on the low energy side (532 to 532.7 eV) attributed to oxygen deterioration and the peak on the high energy side (532.7 to 534 eV) attributed to ozone deterioration. Hence, peak separation was performed and then the contribution rates of oxygen deterioration and ozone deterioration were determined using Equation 3. In this manner, the sample subjected to both oxygen deterioration and ozone deterioration can be analyzed for the proportion of each of the two deterioration factors, oxygen deterioration and ozone deterioration.

In the method for calculating the contribution rates, the contribution rates of oxygen deterioration and ozone deterioration can be similarly determined when peak intensities are used instead of the peak areas in Equation 3.

Still other examples of the deterioration analysis method include a method that includes: determining a normalization constant γ using Equation 4 below based on an X-ray absorption spectrum at the carbon K-shell absorption edge after deterioration; and correcting a total peak area of the oxygen K-shell absorption edge with the normalization constant γ to determine the amount of oxygen and ozone bonded to the polymer material:

[total area of X-ray absorption spectrum at carbon K-shell absorption edge]×γ=1, and

[peak area of oxygen K-shell absorption edge]× γ=amount (index) of oxygen and ozone bonded.      (Equation 4)

In this manner, the amount of oxygen and ozone bonded to a polymer material due to deterioration can be measured and used as a deterioration indicator.

In the method for determining the bonded amount, the total peak area is the integral of the spectrum over a measurement range. The energy range can be changed according to the measurement conditions and the like.

The method for determining the bonded amount is more specifically described using an example in which BR samples subjected to ozone deterioration for an hour and seven hours are used.

Figure 7:
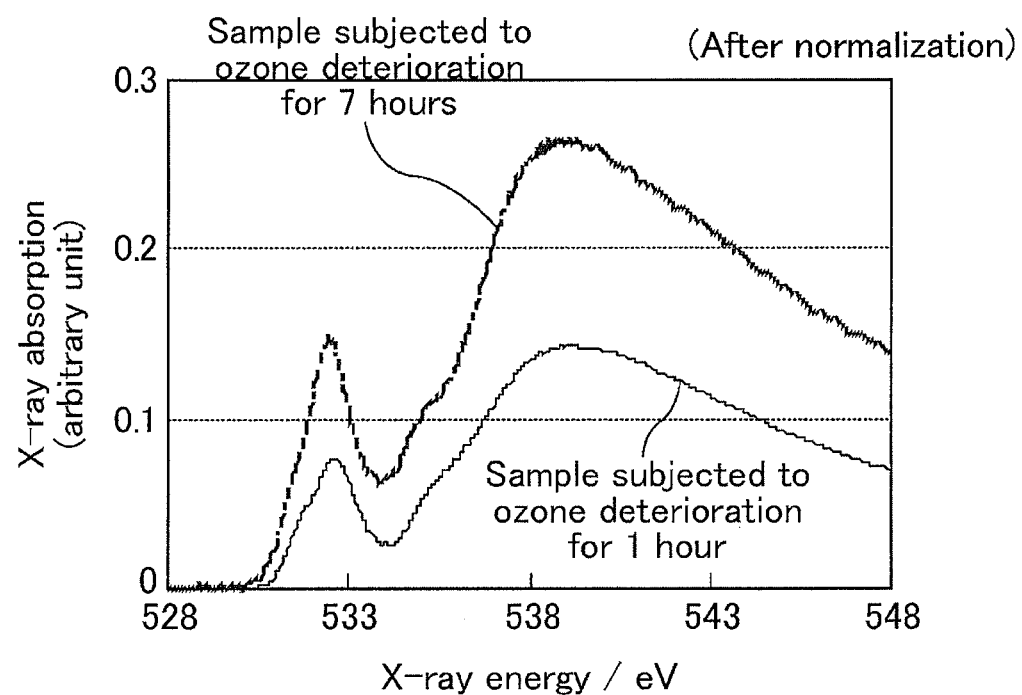
FIG. 7 is a graph (after normalization) showing the results of NEXAFS measurement in butadiene rubber samples subjected to ozone deterioration for one hour and seven hours.

FIG. 7 shows the results of NEXAFS measurement in these samples. These spectra are each obtained by calculating a normalization constant γ using Equation 4 based on an X-ray absorption spectrum at the carbon K-shell absorption edge, and carrying out normalization as mentioned above. The normalized peak area of the oxygen K-shell absorption edge is thought to correspond to the amount of oxygen and ozone bonded. As shown in the figure, the sample subjected to deterioration for seven hours shows a larger area than the sample subjected to deterioration for an hour, and therefore the resulting value can be used as a deterioration index. A larger number of the deterioration index indicates a larger amount of oxygen bonded to the polymer material due to deterioration. In this manner, the deterioration rate when oxygen and ozone are bonded to a polymer material can be measured based on the rate of increase in the peak area of the oxygen K-shell absorption edge.

The method of the present invention mentioned above can be carried out using, for example, the BL12 beamline at Kyushu Synchrotron Light Research Center (SAGA-LS).

The polymer material usable in the present invention is not particularly limited, and may be any conventionally known material. For example, the polymer material may suitably be a rubber material containing at least one diene rubber, or a composite material combining the rubber material and at least one resin. Examples of the diene rubber include polymers containing a double bond, such as natural rubber (NR), isoprene rubber (IR), butadiene rubber (BR), styrene butadiene rubber (SBR), acrylonitrile butadiene rubber (NBR), chloroprene rubber (CR), butyl rubber (IIR), halogenated butyl rubber (X-IIR), and styrene isoprene butadiene rubber (SIBR).

The resin is not particularly limited, and may be a general purpose resin used in the rubber industry field. Examples thereof include petroleum resins such as C5 aliphatic petroleum resins and cyclopentadiene petroleum resins. The deterioration analysis method of the present invention can suitably be applied to these materials.

EXAMPLES

The present invention is more specifically described referring to, but not limited to, examples.

Examples and Comparative Examples

Deteriorated samples used in examples and comparative examples were prepared using the rubber materials and deterioration conditions mentioned below. For measurement by the NEXAFS method, each sample was processed to have a thickness of 100 μm or less using a microtome. Then, to avoid any influence of oxygen other than that due to deterioration, the prepared samples were stored in a vacuum desiccator.
(Rubber Materials)
IR: Nipol IR 2200 from ZEON CORPORATION
BR: Ubepol BR 130B from UBE INDUSTRIES, LTD.
SBR: Nipol 1502 from ZEON CORPORATION
SIBS: SIBSTAR 102T from Kaneka Corporation
Sample after driving in US: Tire that had been driven in US
Sample after driving in Japan: Tire that had been driven in Japan
(Deterioration Conditions)
Ozone deterioration: 40° C., 50 pphm (1 hour or 7 hours)
Oxygen deterioration: 80° C., oxygen:nitrogen=5:1 (168 hours)
(Used Devices)
NEXAFS: NEXAFS measurement device provided with the beamline BL12 at Kyushu Synchrotron Light Research Center (SAGA-LS)
XPS: AXIS Ultra from Kratos Surface Analysis The degree (%) of deterioration of each sample was determined through the following deterioration rate analysis with NEXAFS. Also, the contribution rates (%) of oxygen and ozone deterioration were determined through the following deterioration contribution rate analysis. In addition, the deterioration indicator (index) was determined through the following deterioration indicator determination.

The measurement conditions of NEXAFS used here were as follows.
Brilliance: $5 \times 10^{12}$ photons/s/mrad$^2$/mm$^2$/0.1% bw
Number of photons: $2 \times 10^9$ photons/s
(Deterioration Rate Analysis)

Scanning was performed over a range of high intensity X-ray energies of 260 to 400 eV to obtain X-ray absorption spectra at the carbon K-shell absorption edge. Normalization constants $\alpha$ and $\beta$ were calculated using Equation 1 based on the spectra over the required range of 260 to 350 eV, and then the spectra were normalized (corrected) with the obtained constants. The normalized spectra were subjected to waveform separation, and then the degree (%) of deterioration was determined using Equation 2 based on the resulting peak areas attributed to $\pi^*$ transition at around 285 eV.
(Deterioration Contribution Rate Analysis)

Scanning was performed over a range of high intensity X-ray energies of 500 to 600 eV to obtain an X-ray absorption spectrum at the oxygen K-shell absorption edge. The spectrum was subjected to waveform separation, and then the contribution rates of oxygen deterioration and ozone deterioration were calculated using Equation 3, wherein the oxygen deterioration corresponds to a peak on the low energy side with a peak top at 532 to 532.7 eV, and the ozone deterioration corresponds to a peak on the high energy side with a peak top at 532.7 to 534 eV.
(Deterioration Indicator Determination)

The normalization constant $\gamma$ was determined using Equation 4 based on the X-ray absorption spectrum at the carbon K-shell absorption edge after deterioration obtained in the deterioration rate analysis. The total peak area of the oxygen K-shell absorption edge was corrected (normalized) with the constant, whereby the amount of oxygen and ozone bonded to the polymer material (deterioration indicator) was determined based on Equation 4.

In Comparative Examples 1 to 4, the deteriorated samples were evaluated using XPS.

Table 1 shows the results obtained in the above analyses.

TABLE 1

|  | Comparative Example 1 | Example 1 | Example 2 | Example 3 |
|---|---|---|---|---|
| Measurement method | XPS | NEXAFS | NEXAFS | NEXAFS |
| Material name | IR | IR | IR | IR |
| Deterioration time (h)/ozone | 1 | 1 | 7 | — |
| Deterioration time (h)/hot oxygen | — | — | — | 168 |
| Contribution rate (%) of ozone deterioration | Not calculable | 100 | 100 | 0 |
| Contribution rate (%) of oxygen deterioration | Not calculable | 0 | 0 | 100 |
| Degree (%) of deterioration | Not calculable | 78 | 100 | 23 |
| Deterioration indicator | Not calculable | 0.43 | 0.56 | 0.22 |

|  | Comparative Example 2 | Example 4 | Example 5 | Example 6 |
|---|---|---|---|---|
| Measurement method | XPS | NEXAFS | NEXAFS | NEXAFS |
| Material name | BR | BR | BR | BR |
| Deterioration time (h)/ozone | 1 | 1 | 7 | — |
| Deterioration time (h)/hot oxygen | — | — | — | 168 |
| Contribution rate (%) of ozone deterioration | Not calculable | 100 | 100 | 0 |
| Contribution rate (%) of oxygen deterioration | Not calculable | 0 | 0 | 100 |
| Degree (%) of deterioration | Not calculable | 57 | 88 | 19 |
| Deterioration indicator | Not calculable | 0.22 | 0.43 | 0.40 |

|  | Comparative Example 3 | Example 7 | Example 8 | Example 9 |
|---|---|---|---|---|
| Measurement method | XPS | NEXAFS | NEXAFS | NEXAFS |
| Material name | SBR | SBR | SBR | SBR |
| Deterioration time (h)/ozone | 1 | 1 | 7 | — |
| Deterioration time (h)/hot oxygen | — | — | — | 168 |

TABLE 1-continued

|  |  |  |  |  |
|---|---|---|---|---|
| Contribution rate (%) of ozone deterioration | Not calculable | 100 | 100 | 0 |
| Contribution rate (%) of oxygen deterioration | Not calculable | 0 | 0 | 100 |
| Degree (%) of deterioration | Not calculable | 12 | 37 | 5 |
| Deterioration indicator | Not calculable | 0.18 | 0.25 | 0.10 |

|  | Comparative Example 4 | Example 10 | Example 11 |
|---|---|---|---|
| Measurement method | XPS | NEXAFS | NEXAFS |
| Material name | IR/SIBS | IR/SIBS | IR/SIBS |
| Deterioration time (h)/ozone | 1 | — | 7 |
| Deterioration time (h)/hot oxygen | — | 168 | — |
| Contribution rate (%) of ozone deterioration | Not calculable | 0 | 100 |
| Contribution rate (%) of oxygen deterioration | Not calculable | 100 | 0 |
| Degree (%) of deterioration | Not calculable | 16 | 85 |
| Deterioration indicator | Not calculable | 0.13 | 0.51 |

|  | Example 12 | Example 13 |
|---|---|---|
| Measurement method | NEXAFS | NEXAFS |
| Material name | Sample after driving in US | Sample after driving in Japan |
| Deterioration time (h)/ozone | — | — |
| Deterioration time (h)/hot oxygen | — | — |
| Contribution rate (%) of ozone deterioration | 55 | 10 |
| Contribution rate (%) of oxygen deterioration | 45 | 90 |
| Degree (%) of deterioration | 45 | 25 |
| Deterioration indicator | 0.63 | 0.21 |

In Comparative Examples 1 to 4 using XPS, none of the contribution rates of ozone deterioration and oxygen deterioration, the degree of deterioration and the deterioration indicator (index) of the deteriorated samples could be analyzed. In contrast, in examples using NEXAFS, all of these items could be analyzed. The results shows that, in Examples 1, 2, 4, 5, 7, 8 and 11 subjected to only ozone deterioration, the contribution rate of ozone deterioration was 100%, and, in Examples 3, 6, 9 and 10 subjected to only oxygen deterioration, the contribution rate of oxygen deterioration was 100%. Additionally, the results of the degree of deterioration and the deterioration indicator in these examples had excellent correlations. In Examples 12 and 13 where samples subjected to both ozone deterioration and oxygen deterioration were used, the contribution rate of each deterioration could be analyzed. Therefore, the evaluation according to the present invention was demonstrated to be effective.

The invention claimed is:

1. A deterioration analysis method, comprising
irradiating a polymer material with high intensity X-rays, and measuring X-ray absorption while varying the energy of the X-rays, to analyze deterioration of the polymer,
wherein the polymer material is a rubber material containing at least one diene rubber, or a composite material combining the rubber material and at least one resin,
an energy range scanned with the high intensity X-rays is 4000 eV or less,
the deterioration analysis method comprises: calculating normalization constants $\alpha$ and $\beta$ using Equation 1 below based on X-ray absorption spectra obtained by scanning over a required range of high intensity X-ray energies at the carbon K-shell absorption edge within the range of 260 to 400 eV; performing waveform separation of the X-ray absorption spectra at the carbon K-shell absorption edge corrected with the normalization constants $\alpha$ and $\beta$ to obtain peak areas attributed to $\pi^*$ transition at around 285 eV; and determining a degree of deterioration using Equation 2 below with the obtained peak areas:

[total area of X-ray absorption spectrum over measurement range of sample before deterioration]× $\alpha$=1, and

[total area of X-ray absorption spectrum over measurement range of sample after deterioration]× $\beta$=1; and       (Equation 1)

[1−[(peak area of $\pi^*$ after deterioration)×$\beta$]/[(peak area of $\pi^*$ before deterioration)×$\alpha$]]×100=degree (%) of deterioration.       (Equation 2)

2. The deterioration analysis method according to claim 1, wherein peak intensities are used instead of the peak areas.

3. The deterioration analysis method according to claim 1, wherein the high intensity X-rays have a number of photons of $10^7$ (photons/s) or more and a brilliance of $10^{10}$ (photons/s/mrad$^2$/mm$^2$/0.1% bw) or more.

4. The deterioration analysis method according to claim 2, wherein the high intensity X-rays have a number of photons of $10^7$ (photons/s) or more and a brilliance of $10^{10}$ (photons/s/mrad$^2$/mm$^2$/0.1% bw) or more.

* * * * *